(12) United States Patent
Gourves et al.

(10) Patent No.: US 9,625,363 B2
(45) Date of Patent: Apr. 18, 2017

(54) MEASURING HEAD INTENDED TO BE FITTED TO A DYNAMIC PENETROMETER AND METHOD OF MEASUREMENT USING SUCH A MEASURING HEAD

(71) Applicant: SOL SOLUTION, Riom (FR)

(72) Inventors: Roland Gourves, Marsat (FR); Miguel Benz Navarrete, Clermont Ferrand (FR)

(73) Assignee: SOL SOLUTION, Riom (FR)

( * ) Notice: Subject to any disclaimer, the term of this patent is extended or adjusted under 35 U.S.C. 154(b) by 208 days.

(21) Appl. No.: 14/379,347

(22) PCT Filed: Feb. 22, 2013

(86) PCT No.: PCT/EP2013/053573
§ 371 (c)(1),
(2) Date: Aug. 18, 2014

(87) PCT Pub. No.: WO2013/124426
PCT Pub. Date: Aug. 29, 2013

(65) Prior Publication Data
US 2015/0007640 A1    Jan. 8, 2015

(30) Foreign Application Priority Data

Feb. 23, 2012    (FR) ...................................... 12 51660

(51) Int. Cl.
*G01N 3/30* (2006.01)
*G01N 3/32* (2006.01)
(Continued)

(52) U.S. Cl.
CPC ................. *G01N 3/42* (2013.01); *G01N 3/30* (2013.01); *G01N 3/32* (2013.01); *G01V 99/00* (2013.01); *G01N 2203/0676* (2013.01)

(58) Field of Classification Search
CPC .. G01N 3/00; G01N 3/30; G01N 3/32; G01N 3/34; G01N 3/36; G01N 3/42;
(Continued)

(56) References Cited

U.S. PATENT DOCUMENTS

| 4,116,041 A | 9/1978 | Tholen et al. |
| 4,332,160 A | 6/1982 | Baragar et al. |

(Continued)

FOREIGN PATENT DOCUMENTS

| FR | 2 732 246 | 10/1996 |
| FR | 2 817 344 | 5/2002 |

(Continued)

OTHER PUBLICATIONS

International Search Report dated Mar. 27, 2013, corresponding to PCT/EP2013/053573.

*Primary Examiner* — Nguyen Ha
(74) *Attorney, Agent, or Firm* — Young & Thompson

(57) ABSTRACT

A measuring head, intended to be fitted to a dynamic penetrometer, and attached to a drill string provided with a tip, includes a driving head intended to receive an impact to be transmitted, via the rest of the measuring head, to the drill string; and a central rod for transmitting the impact from the driving head to the drill string, the central rod having a first end turned towards the driving head, and a second end opposite the first end, and suitable for engaging with the drill string, the central rod being provided with at least one deformation sensor. It includes at least one absorption member interposed between an impact receiving end portion of the driving head and the second end of the central rod and which is suitable for filtering the wave transmitted to the drill string when the end portion of the driving head receives an impact.

20 Claims, 5 Drawing Sheets

Figure 1:
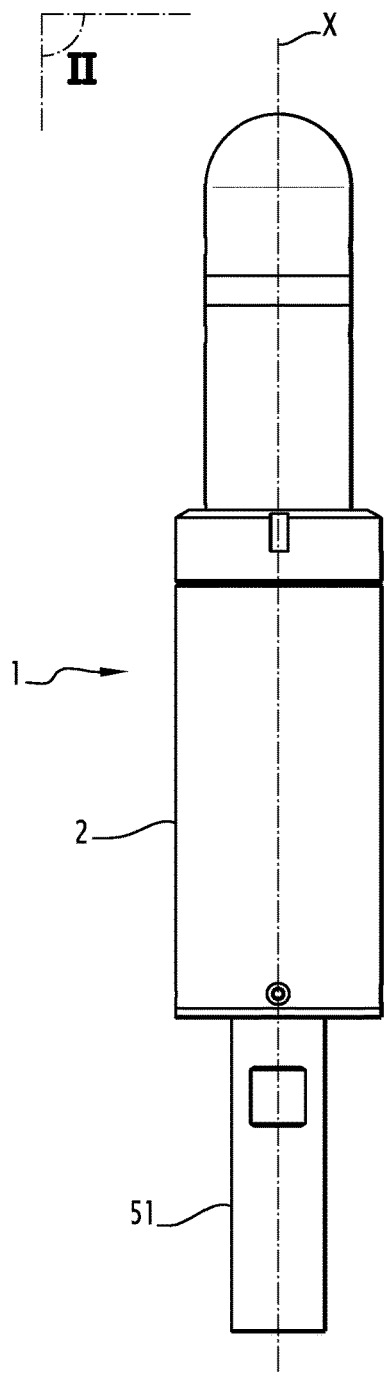

(51) Int. Cl.
*G01N 3/42* (2006.01)
*G01V 99/00* (2009.01)

(58) Field of Classification Search
CPC ...... G01N 29/00; G01N 29/04; G01N 29/045; G01N 2203/0676; G01V 99/00
See application file for complete search history.

(56) References Cited

U.S. PATENT DOCUMENTS

| | | | | |
|---|---|---|---|---|
| 7,581,446 B2 * | 9/2009 | Troxler | ............... | G01N 33/42 |
| | | | | 367/14 |
| 2008/0307863 A1 * | 12/2008 | Sercel | ............... | G01N 3/303 |
| | | | | 73/84 |

FOREIGN PATENT DOCUMENTS

| | | | | |
|---|---|---|---|---|
| FR | 2 938 276 | 5/2010 | | |
| GB | 476842 A | * 12/1937 | ............ | G01N 3/303 |
| WO | 03/056302 | 7/2003 | | |

* cited by examiner

MEASURING HEAD INTENDED TO BE FITTED TO A DYNAMIC PENETROMETER AND METHOD OF MEASUREMENT USING SUCH A MEASURING HEAD

BACKGROUND OF THE INVENTION

This invention relates to a measuring head intended to be fitted to a dynamic penetrometer as well as a method of measurement using such a measuring head.

DESCRIPTION OF THE RELATED ART

A dynamic penetrometer is a device that makes it possible to measure, in situ, the mechanical characteristics of the ground without it being necessary to take a sample for study in a laboratory.

A penetrometer comprises a string of metal rods. The free end of an end rod is provided with a tip which provides for the penetrating into the ground of a portion of the rod string when an impact is exerted on the free end of the other end rod of the rod string. This impact is transmitted to the rod string by the intermediary of a driving head.

Such a dynamic penetrometer is described in FR-A-2 817 344 and marketed by the company SOL SOLUTION. This penetrometer makes it possible to measure the compactness of the ground and comprises a driving head, a central rod, a tapered probe and a rod string connecting the driving head to the tapered probe. The operation of the penetrometer is based on the principle consisting in providing energy to the driving head, in particular via a hammer strike. This energy is then transmitted by the central rod to the rod string linked to the tapered probe. The latter is then driven into the ground to a depth depending on the density of the ground. Knowing the energy provided to the penetrometer, the value of the displacement of the probe and the section of the probe, it is then possible to determine the level of compactness of the ground. The last two characteristics can be measured easily and the energy transmitted to the penetrometer is measured by the intermediary of a sensor of the piezoelectric type of which the deformation generates an electric signal that is proportional to the intensity of the impact. In order to measure the energy supplied to the penetrometer, strain gauges mounted as a Wheatstone bridge can also be used. The strain gauges are then placed under tension and their electrical resistance varies according to the deformation of the gauge. The electric signal, applied to the strain gauges, therefore varies in proportion to the intensity of the impact and makes it possible to deduce the value of the energy transmitted to the driving head. In this document of prior art, concern is not given to measuring the wave transmitted during the impact and even less to filtering such a transmitted wave.

The utilisation of such a penetrometer is limited. Indeed, the impact is, generally, carried out manually using a hammer. Because of this, measuring the characteristics of the ground is carried out at a limited depth, typically between 0 and 7 m.

In addition, measuring the energy supplied to the penetrometer lacks in precision and using a piezoelectric material such as quartz increases the cost of the penetrometer.

SUMMARY OF THE INVENTION

The invention intends to overcome more particularly these disadvantages by proposing a measuring head intended to be fitted on a dynamic penetrometer allowing for the determination, reliably, of the characteristics of the ground by optimising the collection and the processing of the signals provided by a penetrometer, and this for thicknesses of ground ranging up to 15 m.

The presence of an absorption member able to filter the shock wave allows for an optimised collection of the signals while still limiting the processing of the latter, with the signals as such being subjected to a first filtration.

BRIEF DESCRIPTION OF THE DRAWING FIGURES

Figure 2:
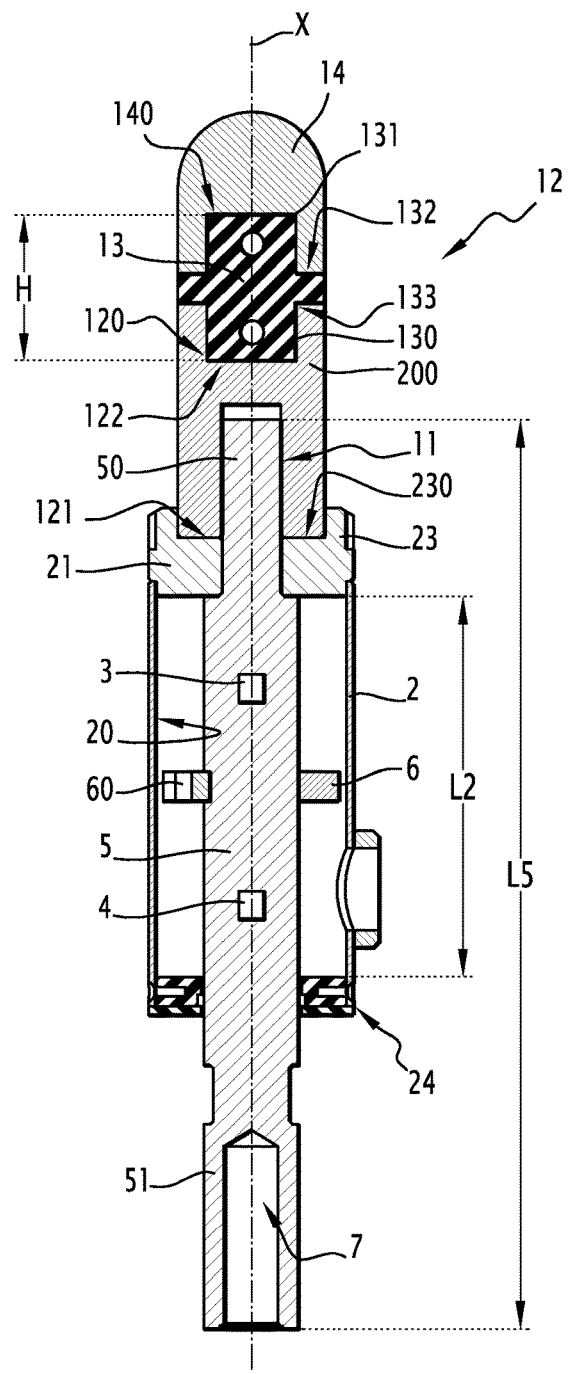
Figure 3:
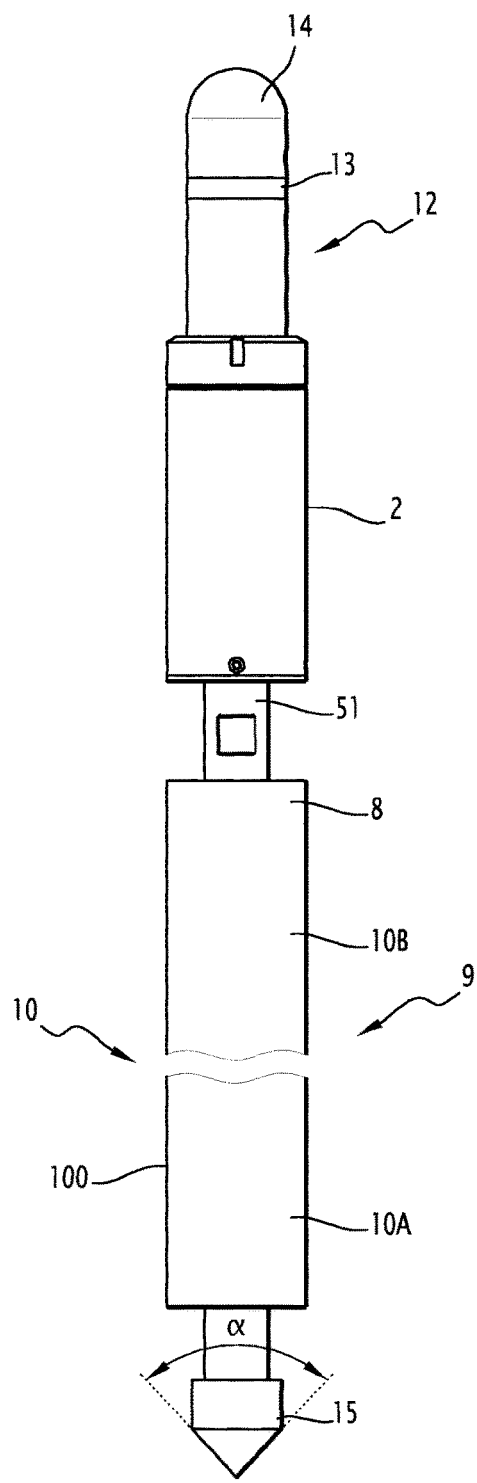
Figure 4:
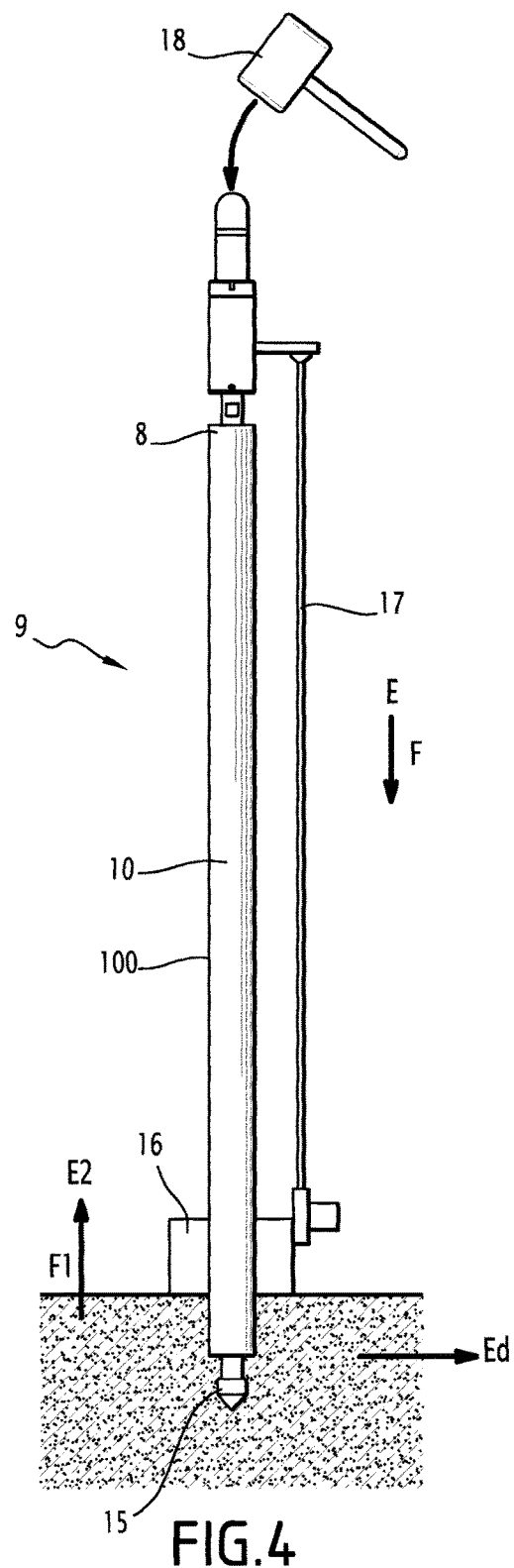
Figure 5:
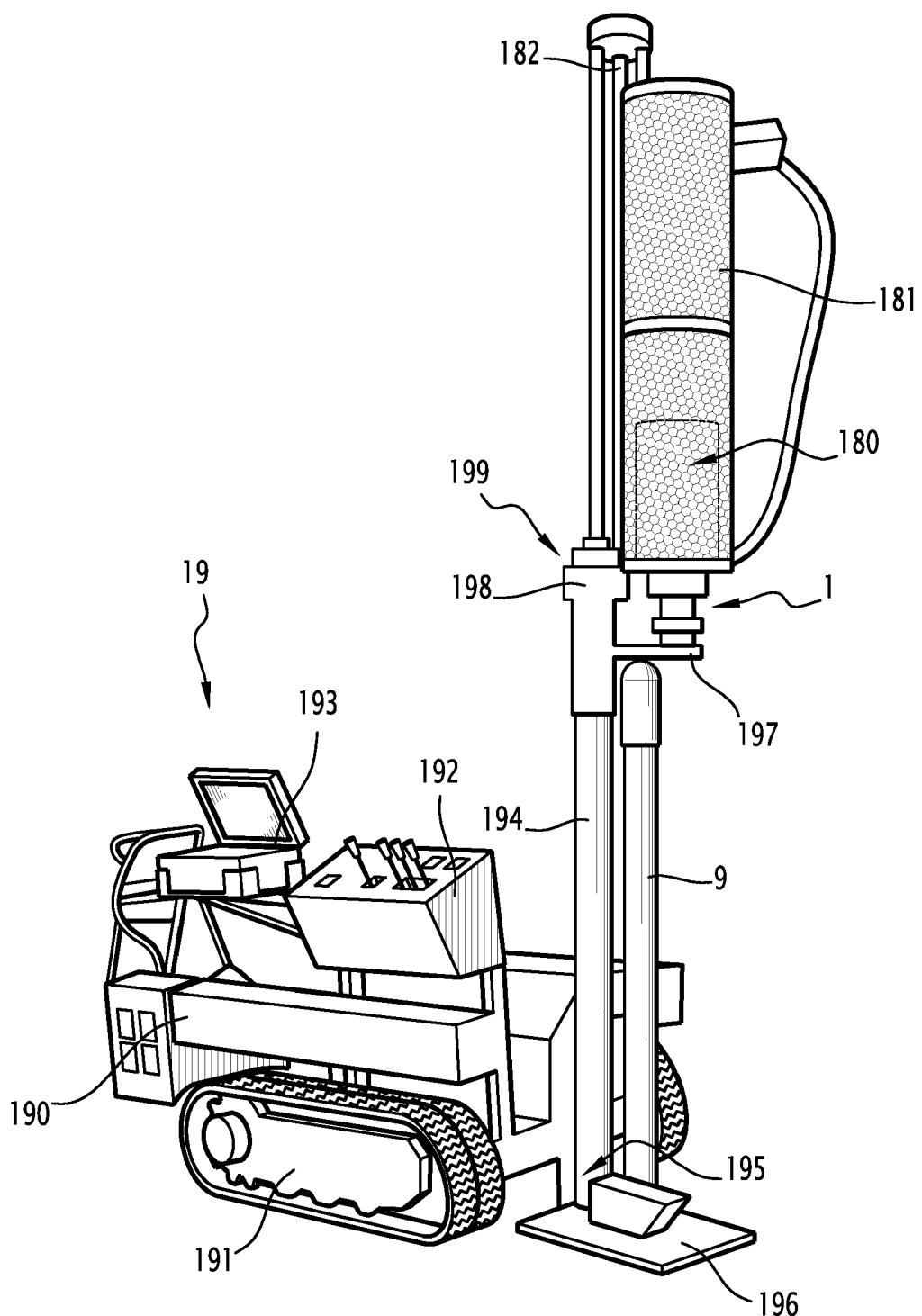
Figure 6:
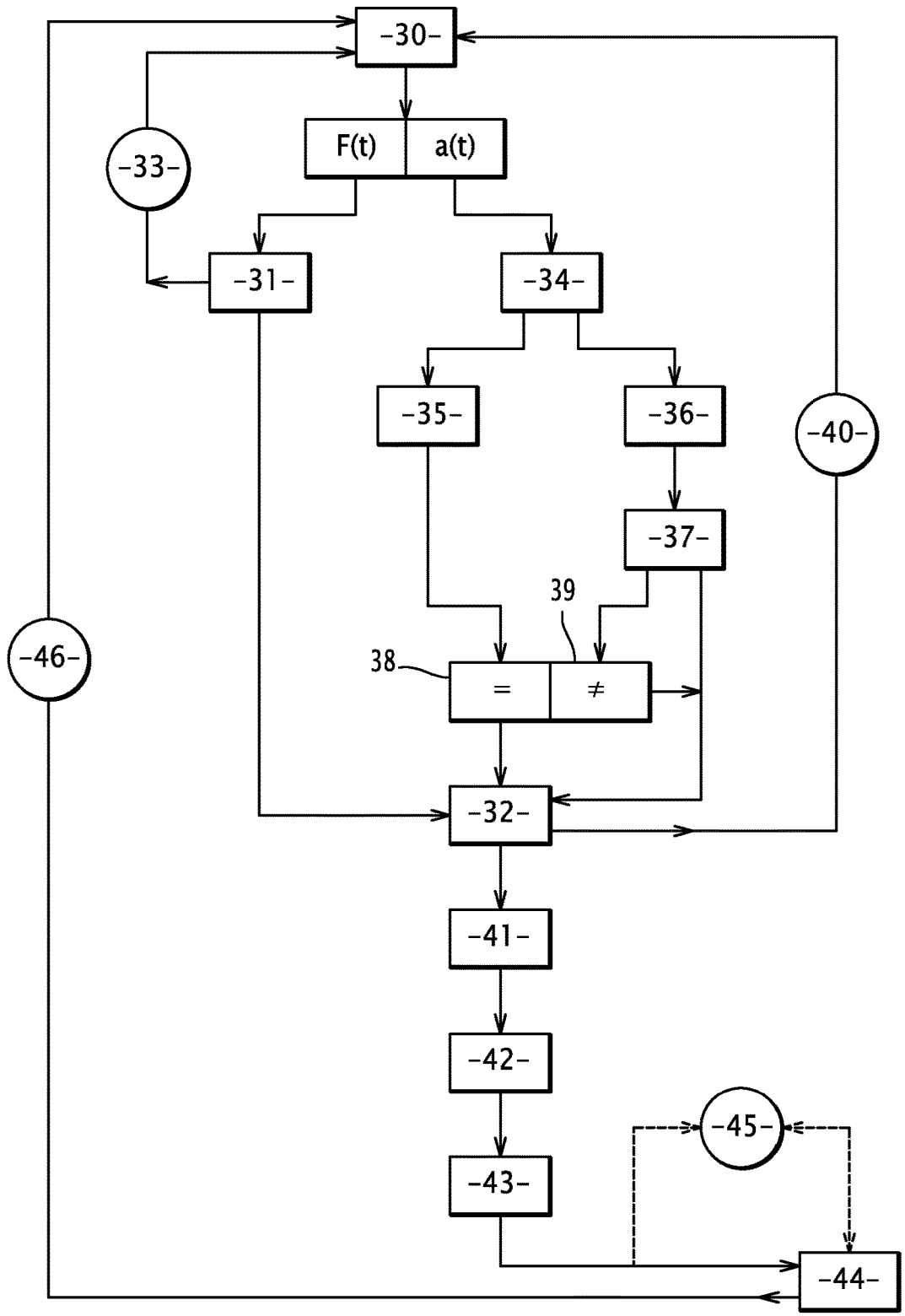
Figure 7:
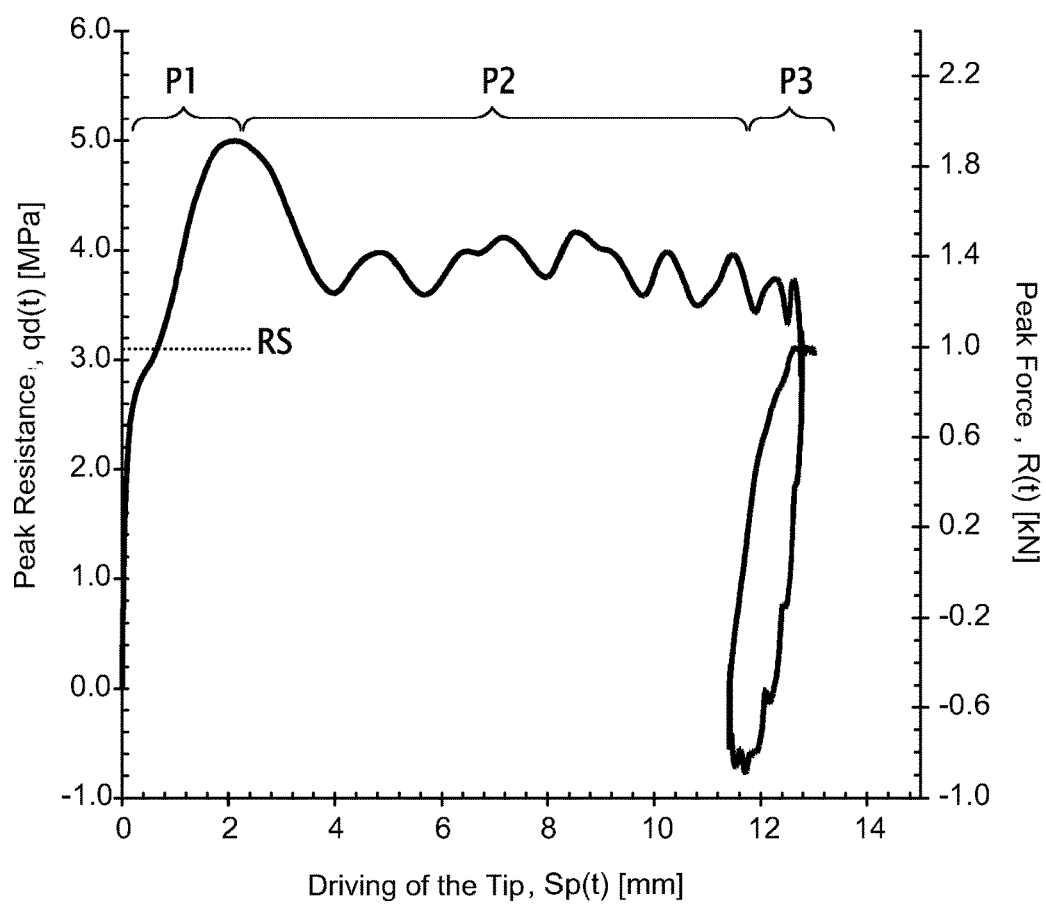

The invention shall be better understood and other advantages of the latter shall appear more clearly when reading the following description of a measuring head carried out in accordance with the invention, provided solely by way of example and made in reference to the annexed drawings wherein:

FIG. 1 is a side view of a measuring head in accordance with the invention,

FIG. 2 is a longitudinal cross-section, on the same scale, according to the plane II of the measuring head of FIG. 1, FIG. 3 is a simplified side view on another scale of the measuring head of FIG. 1 connected to a rod string of a penetrometer, with this rod string being partially shown, FIG. 4 is a simplified side view of a first type of penetrometer provided with the measuring head of FIG. 1, with a hammer shown in front position before an impact on the driving head, with the ground being shown diagrammatically, FIG. 5 is a simplified perspective view on a smaller scale of another type of penetrometer provided with the measuring head of FIG. 1, FIG. 6 is a diagram that shows the method of processing the signals collected by the measuring head and FIG. 7 is a simplified curve of the signals collected by such measuring head representing, once processed, the behaviour of the ground.

DETAILED DESCRIPTION OF THE INVENTION

As is shown in FIGS. 1 and 2, the measuring head 1 comprises a cylindrical main body 2 with a circular base. This hollow body 2 is made of steel. Alternatively, it is made of another rigid material.

At least one, advantageously two deformation sensors 3, 4, diagrammatically shown in FIG. 2, are mounted on a central rod 5 inserted longitudinally into the hollow body 2 of the measuring head 1. The central rod 5 is solid and cylindrical and has a circular base. Its main longitudinal axis X is confounded with the main longitudinal axis of the body 2 when it is inserted into the latter.

The two deformation sensors 3, 4, also referred to as strain gauges, are aligned according to the axis X and arranged in relation to one another at a distance between 10% and 50% of the useful length L2 of the main body 2.

Advantageously, as shown in FIG. 2, an accelerometer 6 is also arranged on the rod 5 between the two strain gauges 3, 4. The reference portion 60 of the accelerometer 6 is fastened onto the inner wall 20 of the hollow body 2.

The rod 5 has a length L5 such that it exceeds the main body 2 by these two ends 50, 51. The ends 50, 51 extend beyond the body 2 by passing through seals 21, 22 that close the ends 23, 24 of the body 2. The seals 21, 22 provide, on the one hand, the seal in relation to dust and water for the interior of the body 2 and, on the other hand, make it possible to limit the electromagnetic disturbances on the measuring head 1, by insulating the electrical and electronic elements, for example the sensors 3, 4 and the accelerometer 6, inserted in the main body 2. The body 2 also participates, via the nature of the material it is comprised of, in the electromagnetic protection of the elements that it contains.

Outputs, not shown, allowing for the connection of the various sensors to a calculation module, are also provided on the main body 2 of the measuring head 1.

The end 51, referred to as bottom when viewing FIG. 2, of the rod 5 forms the end of the measuring head. It comprises a blind hole 7. The hole 7 is made longitudinally in the end 51 and it is centred on the axis X of the rod 5. The hole 7 allows for the fastening of the measuring head 1, via nesting of the male/female type, known per se, onto an end 8 of a string 9 of rods 10, as shown in FIG. 3. The string 9 of rods 10 also extends according to the axis X of the central rod 5 and the end 51 is, in configuration for use of the penetrometer, directed towards the ground. This fastening can be definitive. In this case, the first rod 10 of the string 9 is, for example, welded to the measuring head, with the hole 7 being adapted to such a fastening. Alternatively, the fastening is carried out in a detachable manner, for example by screwing, with the hole 7 then being threaded. A detachable fastening makes it possible to mount such a measuring head 1 "as retrofitting" on a penetrometer provided with a string 9 of rods 10. More generally, the end 51 of the rod 5 is suitable for engaging mechanically with the string 9 of rods 10.

The upper end 50 of the rod 5, when viewing FIG. 2, is, similarly to the lower end 51, located outside of the main body 2 beyond the seal 21. The end 50 is inserted into a blind hole 11 arranged in the main body 200 of a driving head 12.

More generally, the end 50 of the rod 5 is suitable for engaging mechanically with the driving head 12. The hole 11 is carried out in the central position, according to a direction parallel to a longitudinal axis of the driving head 12. The body 200 of the driving head 12 has the shape of an elongated cylinder with a circular base. Its dimensions are adapted so that, when the end 50 is in the hole 11, the longitudinal axis of the driving head 12 is aligned with the axis X of the body 2. Consequently, the driving head 12, the central rod 5 and the string 9 of rods 10 are all aligned according to the axis X.

From the top to the bottom in FIG. 1, the driving head 12, then the central rod 5 and finally the string 9 of rods 10 can then be found.

The hole 11 is arranged in an end 121 of the body 200 received in a counterbore 230 made in the seal 21. The free end 120 opposite the end 121, is suitable for receiving an absorption member 13 comprising a material adapted in order to provide for a filtering of the waves transmitted to the string 9 of rods 10. This material is, advantageously, a high-impact polymer or high-density polyethylene. Alternatively, this is another material, for example rubber. This member 13 is configured as a solid disc covering the end 120. The member 13 comprises, in central position, two reliefs 130, 131 arranged facing one another on two faces 132, 133 opposite the member 13 and perpendicular to these faces. Alternatively, the member 13 is configured as a ring, as a double ring, as a solid disc without relief or as any other shape suited to the configuration of the measuring head and/or of the filtering desired.

Moreover, the material comprising the member 13 and/or geometrical configuration participate in the electromagnetic protection of the measuring head 1.

The relief 130 is inserted into a housing 122 arranged in the end 120. The relief 131 is inserted into a housing 140 arranged in an end portion 14 of the driving head 12, solid and configured substantially as a half-moon. This end portion 14 forms the portion of the driving head 12 intended to receive the impact. The latter is transmitted, via the member 13 and the rod 5, to all of the string 9 of rods 10 of the penetrometer. The absorption member 13 is therefore interposed, according to the axis X, between the end portion 14 of the driving head 12 and the end 51 of the central rod 5. As the sensors 3 and 4 are arranged on the central rod 5, they are therefore positioned between the absorption member 13 and the end 51 of the rod 5. The height H of the absorption member 13 is advantageously between 10 and 100 mm, with this height being taken between the reliefs 130 and 131 included. The density of the member 13, de facto the density of the material comprising the member 13 is between ¼ and ¾ of the density of steel. Advantageously, the density of the member 13 is between ⅓ and ½ of the density of steel and, preferably, in the neighbourhood of ⅓ of the density of steel.

The end 50 of the rod 5 is inserted into the blind hole 11 of the body 200 of the driving head 12 with clearance. In other terms, the end 50 is not in contact with the bottom of the blind hole 11. This also participates in the absorption during an impact exerted on the portion 14.

The configuration of the head 12, in particular of the portion 14 and of the member 13, makes it possible to carry out an impact plastic and to generate a wave, sinusoidal or not, that is wider than that usually generated with a penetrometer of prior art. In other terms, the member 13 absorbs certain frequencies of the wave referred to as descending, i.e. of the wave generated by the impact and directed towards the string 9 of rods 10.

The presence of the member 13 as such makes it possible to generate an impact and a shock wave of a given type. It also participates in protecting the measuring head 1 in terms of electromagnetic disturbances.

FIG. 3 shows a string 9 of rods 10 provided with the measuring head 1. The bottom end 7 of the measuring head 1 is connected to an end rod 10 made of steel, definitively or in a detachable manner, of a string 9 of rods 10. The string 9 has a length defined by the number of rods 10 and/or the length of each rod 10, for the type of tests to be carried out. In general with a so-called hand penetrometer, i.e. a variable energy dynamic penetrometer of which the driving head is intended to receive a variable impact exerted manually, this length is between 0.25 m and 1 m.

The end rod 10A, located in bottom position when viewing FIG. 3, is provided with a tip 15. The geometry of this tip 15, also made of steel, is adapted so that the latter is tapered with an angle α at the top of at least 60° and, preferably, in the neighbourhood of 90°. The active portion of a variable energy dynamic penetrometer therefore comprises a string 9 of rods 10 of which an end rod 10A comprises a tip 15 and another end rod 10B a measuring head 1.

Such a so-called hand penetrometer is shown in FIG. 4. This type of penetrometer is easy to transport. It is shown in active configuration, installed vertically and perpendicularly to the ground by the intermediary of a guide 16, configured as a pierced plate, allowing for the precise positioning of the tip 15 before it is driven into the ground.

In FIGS. 3 and 4, a sheath 100 surrounds the string 9 of rods 10. This sheath 100 prevents the direct contact between the ground and the rods 10. As such, only, the tip 15 is in contact with the ground, with the latter as such exerting no friction on the rods 10 that can distort the measurements. In another embodiment, according to the nature of the ground, the penetrometer is devoid of a sheath 100.

The top end 8 of the top rod 10B of the string 9 of rods is provided with the measuring head 1 which is connected to the guide 16 by a belt 17 which makes it possible to measure the distance travelled by the tip 15 when it is driven in when an impact is applied on the rounded portion 14 of the driving head 12. At the time of this impact, carried out using a hammer 18 of which certain characteristics are known, an impact plastic is carried out on the portion 14. At the time of this impact, the portion 14 transmits to the rod 5 and to the tip 15, via the string 9 of rods, an energy E from top to bottom, according to an arrow F, allowing the tip 15 of the penetrometer to be driven in the ground. A portion Ed of this energy E is dissipated in the ground, according to the nature and the characteristics of the latter. Another portion Er of the energy E is reflected and transmitted by the tip 15 in the opposite direction, i.e. from bottom to top according to the arrow F1, to the measuring head 1 by the string 9 of rods 10.

The reflecting of the energy Er is carried out in a manner similar to the transmission of the energy E, due to the homogeneous properties of the rods 10 all along the string 9 and of the measuring head 1, with these elements being made from the same material, steel.

The presence of the member 13 makes it possible to generate descending waves that are wider than those generated in the absence of the member 13, and this while still filtering certain frequencies corresponding to so-called unwanted waves.

The descending waves are, at least partially, reflected in the direction of the head 1 from the tip 15. These waves are representative of the behaviour of the penetrometer between the tip 15 and the ground and between the portion of the end rod 10A driven into the ground and the ground, over the portion of rod 10A inserted into the ground. In other terms, these waves are the bearers of much information relating to the mechanical behaviour of the ground.

It is therefore interesting to process such waves in order to determine characteristics of the ground that until now could not be determined or at least were not able to be determined reliably and repetitively with a penetrometer of prior art.

FIG. 5 shows another embodiment of the invention with a so-called heavy penetrometer. This is a motorised, self-propelled dynamic constant-energy penetrometer 19, able to carry out tests over substantial depths of ground, typically beyond 5 m, with these tests able to be carried out to depths in the neighbourhood of 15 m.

This type of penetrometer 19 comprises a frame 190 provided with members that provide for the displacement of the penetrometer, in the form of crawler tracks 191. This frame 190, in addition to a module 192 for controlling the penetrometer, also comprises a module 193 for collecting and processing the signals collected by the measuring head 1.

The latter, as hereinabove, is arranged at the end of a string 9 of rods 10, guided along a mast 194 maintained in vertical position during the tests.

The lower end 195 of the mast 194 bears against a guide plate 196 that provides the guiding of the tip 15 in the ground.

The measuring head 1 is arranged offset in relation to the longitudinal axis X of the string 9 of rods 10. It is connected to the string 9 by a plate 197 fixed radially on the outer wall of a sleeve 198. This sleeve 198 is mounted slidingly on the mast 194, from the end 199 of the latter opposite the end 195. A mass 180 is inserted in a sheath 181 for guiding arranged parallel to the mast 194. The mass 180 is set into action via a cylinder 182 inserted into the end 199 of the mast 194. The masse 180 is dropped from a determined height, in the sheath 181, before striking the measuring head 1.

As such, with such a heavy penetrometer 19, it is possible to easily qualify the energy transmitted during the impact since the mass and the speed of falling of the mass 180 are known and defined before each series of measurements. As hereinabove, the measuring head 1 can be provided definitively or in a detachable manner on such a penetrometer 19.

Note that, in the preferred embodiment, two strain gauges 3, 4 are used rather than one which makes it possible, using two deformation measurements and the determining of the driving distance to determine, via calculation, the acceleration without requiring the presence of an accelerometer 6. The latter can however, as shown in FIG. 2, be provided in the measuring head 1, in order to form a backup measurement device in the event of failure of one of the gauges 3 or 4 or in order to carry out a redundant measurement of acceleration.

The measuring head 1, whether it is fastened to a penetrometer of the type of FIG. 4 or of FIG. 5, allows for the collecting of various signals. A first group of signals comprises data concerning the deformation of the string 9 of rods 10 during the transmission of the shockwave from the driving head 12 to the tip 15. These signals represent the resistive force Fp(t) of the tip. The measuring, either direct by the accelerometer 6 or via calculation, of the acceleration a(t) makes it possible to determine the driving speed Vp(t) of the tip 15 as well as the value for the driving Sp(t) of the tip 15 in the ground. It is as such possible to determine the resistance of the ground on the tip 15, by the difference between the energy EFdp(t) transmitted to the ground by the tip 15 and the energy reflected by the tip 15.

The energy EFdp(t), in the form of a compression wave, is transmitted from the driving head 12 to the tip 15 then partially reflected towards the source, i.e. towards the measuring head 1 while a portion is absorbed by the tip and the ground when the penetrometer is driven in. When this reflected wave arrives on the measuring head 1, it is again reflected, this time in the direction of the tip 15. This yoyo phenomenon of the wave continues while decreasing in intensity at each reflection by the tip 15 or the measuring head 1, until it is no longer perceptible.

All of these signals are collected in real time, at each passing of the wave on the measuring head 1. As measurements are taken at about every two microseconds, these signals show, over the period of one measurement, a substantial mass of information.

This information represents the mechanical behaviour of the ground. In particular, the plasticity, elasticity and the shock absorbing of the ground.

In order to carry out the determination of these characteristics using all of the signals collected by a measuring head 1, whether it is mounted on a variable- or constant-energy dynamic penetrometer such as shown in FIGS. 4 and 5, a discrimination needs to be made between the signals that represent characteristics of the ground and the unwanted signals. This is possible, in part, thanks to the absorption member 13 and to the geometric configuration of the portion 14 of the driving head 12. In other terms, a mechanical filtering of certain frequencies of the shockwave is carried out by the measuring head 1.

This mechanical filtering is supplemented by a method of measurement of data collected by the measuring head 1 shown in FIG. 6. Here, the expression "method of measurement" must be understood as designating the collecting of data by the measuring head 1 as well as the processing and the interpreting of this data, with the understanding that the term signal is considered to be a synonym of data.

The method of measurement makes it possible, among other things, to process signals in order to improve the readability of the latter, in addition to the action of the member 13 then, using these processed signals, to interpret them and to determine the characteristics of the ground for example, via comparison for some of them.

The first step 30 consists, using the measuring head 1, in acquiring and in conditioning the signals provided by the sensors 3, 4. Signals F(t) and a(t) are obtained. These signals then undergo a series of processing carried out by a calculation module 193 and different according to the F(t) or a(t) signal.

The resistive force signal F(t) is subjected to, during a step 31, a filtration at 50 Hz in order to remove the electrical noise and a smoothing in order to raise the baseline. In step 32, a corrected signal F(t) is obtained. If after the step 31 the signal is not corrected or cannot be corrected because it is too weak, a new signal F(t) is to be acquired, as indicated by the arrow 33, by repeating the acquisition of new signals during another step 30. The signal of acceleration a(t) is subjected to, during a step 34 a smoothing and a filtering at 50 Hz for the background noise, followed by a correction, at least of the first degree, of the baseline.

To the a(t) signal is then applied a temporal integration processing 35 and a frequency integration processing 36, via fast Fourier transformation, followed by filtering steps 37.

If the values 38, 39 of the signal a(t) obtained respectively at the end of the steps 35 and 37 are identical, in the step 32 a corrected signal a(t) is obtained.

If the values 38, 39 are different, favour is given to the value 39 obtained in the step 37 and this value is considered as being the corrected signal a(t) in the step 32.

If the values of a(t) are visibly in error or too low, a series of measurements is taken again as indicated by the arrow 40.

On the corrected signals F(t) and a(t) obtained in the step 32, a decoupling of the ascending and descending waves is carried out during a step 41. This step is followed by a step 42 of determining the speed of propagation of the compression wave in the ground. This involves determining the impact polar and then the swiftness. This value is characteristic of the behaviour of the ground under the effect of a compression wave.

These corrections make it possible, during a step 43, to reconstruct the peak resistance signals qd(t) as MPa, the peak force R(t) as kN and of the driving of the tip Sp(t) as mm and to show these graphically. An example of such a curve is provided in FIG. 7.

These signals, corrected and able to be used, are either displayed and compared, during a step 44, with the signals from known ground listed in a database, or stored for later processing during a step 45. Note that the storage 45 also intervenes after the step 44.

At each measurement campaign, the signals collected in the step 43, through incrementing, enrich the database.

In parallel to the storage and/or the comparison with the known values, another series of measurements is taken, as shown diagrammatically by the arrow 46.

FIG. 7 shows the characteristics determined in the step 43 after the method of measurement of collected signals. Here, this is an illustration of the behaviour of a ground where, according to the driving of the tip in mm, the resistance at the tip qd(t) and also the peak force in R(t) are represented.

A first portion P1 of the curve is said to be dynamic. It corresponds to the impact on the tip 15, i.e. to the driving of the penetrometer into the ground. This portion P1 characterises the elasticity of the ground.

Then a second portion P2 corresponds to the absorbing of the impact i.e. to the slowing down of the penetration of the tip in the ground. The portion P2 lasts substantially throughout the entire duration of the driving in. This is a characterisation of the plasticity. Analysing this portion P2 also makes it possible to obtain information on the granulometry of the ground, for example via an analysis of the signal.

The last portion P3 is a loop corresponding to a loading and reloading cycle. This is a characterisation of the "pure" elasticity, i.e. the elasticity due solely of the vibrations of the tip 15 in the ground, without interaction of the viscosity of the ground.

Note that FIG. 7 is a simplified representation, in order to facilitate reading the curve.

By comparing the characteristics obtained with the characteristics that are known and stored in a database, it is possible to associate the characteristics of this ground with its nature and/or it composition and/or its granulometry.

The measuring head 1 makes it possible to determine together, i.e. during a series of measurements, these characteristics and this at the time of each impact. By processing the signal and modelling, the signals collected as such make it possible to obtain a substantial amount of information on the mechanical properties of the ground. The static resistance or ultimate resistance Rs of the ground can be determined, for example. Other characteristics are able to be determined by such a measuring head and such a method.

The invention claimed is:

1. A measuring head, intended to be provided on a dynamic penetrometer and suitable to be connected to a string of rods provided with an end tip, this measuring head comprising:
    a driving head intended to receive an impact to be transmitted, via the rest of the measuring head, to the string of rods, the end tip being suitable for being driven into the ground when an impact is applied on the driving head,
    a central rod for transmitting the impact from the driving head to the string, said central rod has a first end, which is turned towards the driving head, and a second end, which is opposite to the first end and which is suitable for engaging with the string, and said central rod is provided with at least one deformation sensor, for collecting signals that are representative of the variations of the resistive force at the end tip and of the acceleration during the driving of the end tip in the ground under the effect of the impact on the driving head, and
    at least one absorption member, which is interposed between an end impact receiving portion of the driving head and the second end of the central rod and which is suitable for filtering a wave transmitted to the string when the end impact receiving portion of the driving head receives the impact.

2. The measuring head according to claim 1, wherein the at least absorption member is made from a material comprising a high-impact polymer or high-density polyethylene.

3. The measuring head according to claim 1, wherein the at least absorption member is received in two housings arranged respectively in the end impact receiving portion of the driving head and in another portion of the driving head.

4. The measuring head according to claim 1, wherein the central rod is furthermore provided with an acceleration sensor.

5. The measuring head according to claim 4, wherein two deformation sensors are arranged one behind the other on the central rod which is inserted in length, and wherein the central rod is inserted into a hollow body of the measuring head, receiving the sensors and limiting the electromagnetic disturbances.

6. The measuring head according to claim 1, wherein the first end of the central rod is inserted into a blind hole arranged in the driving head and wherein the second end of the central rod comprises a blind hole wherein is inserted an end of the string of rods.

7. The measuring head according to claim 1, wherein the central rod comprises a connecting member suitable for connecting the measuring head to the string of rods of the dynamic penetrometer.

8. The measuring head according to claim 1, wherein the end impact receiving portion of the driving head is configured to generate a shockwave.

9. The measuring head according to claim 8, wherein the end impact receiving portion is in the form of a half-moon.

10. The measuring head according to claim 1, wherein the measuring head is adapted to be connected to a string of rods having an end tip which is tapered, with the angle at the top of the end tip being at least 60°.

11. A method of measurement using a dynamic penetrometer provided with such a measuring head in accordance with claim 1, the method comprising at least the following steps:
 a) generating an impact on the end impact receiving portion of the driving head;
 b) collecting, using said at least one deformation sensor, resistive force signals and acceleration signals that are respectively representative of the variations of a resistive force at the end tip and of acceleration during the driving of the end tip in the ground under the effect of the impact on the driving head;
 c) carrying out a frequency filtering of the resistive force signals;
 d) carrying out a temporal filtering and a frequency filtering of the acceleration signals;
 e) validating through comparison of the filtrations carried out in step d);
 f) considering the signals obtained in steps c) and d) as corrected signals;
 g) carrying out a decoupling of the waves on the corrected signals;
 h) determining a speed of propagation or swiftness of a compression wave in the ground;
 i) reconstructing signals concerning the impact received at the end tip (15) of the dynamic penetrometer;
 j) creating a curve that represents the mechanical behaviour of the ground; and
 k) comparing these characteristics with those of known ground and deducing the mechanical behaviour of the ground.

12. The method of measurement according to claim 11, wherein, at step j), the curve is created using resistance characteristics, viscosity and plasticity of the ground.

13. A measuring head, intended to be provided on a dynamic penetrometer and suitable to be connected to a string of rods provided with an end tip, this measuring head comprising:
 a driving head intended to receive an impact to be transmitted, via the rest of the measuring head, to the string of rods;
 a central rod for transmitting the impact from the driving head to the string, said central rod has a first end, which is turned towards the driving head, and a second end, which is opposite to the first end and which is suitable for engaging with the string, and said central rod is provided with at least one deformation sensor; and
 at least one absorption member, which is interposed between an end impact receiving portion of the driving head and the second end of the central rod and which is suitable for filtering a wave transmitted to the string when the end impact receiving portion of the driving head receives the impact,
 wherein the at least absorption member is received in two housings arranged respectively in the end impact receiving portion of the driving head and in another portion of the driving head.

14. The measuring head according to claim 13, wherein the at least absorption member is made from a material comprising a high-impact polymer or high-density polyethylene.

15. The measuring head according to claim 13, wherein the central rod is furthermore provided with an acceleration sensor.

16. The measuring head according to claim 15, wherein two deformation sensors are arranged one behind the other on the central rod which is inserted in length, and wherein the central rod is inserted into a hollow body of the measuring head, receiving the sensors and limiting the electromagnetic disturbances.

17. The measuring head according to claim 13, wherein the central rod comprises a connecting member suitable for connecting the measuring head to the string of rods of the dynamic penetrometer.

18. The measuring head according to claim 13, wherein the end impact receiving portion of the driving head is configured to generate a shockwave.

19. The measuring head according to claim 18, wherein the end impact receiving portion is in the form of a half-moon.

20. The measuring head, intended to be provided on a dynamic penetrometer and suitable to be connected to a string of rods provided with an end tip, this measuring head comprising:
 a driving head intended to receive an impact to be transmitted, via the rest of the measuring head, to the string of rods;
 a central rod for transmitting the impact from the driving head to the string, said central rod has a first end, which is turned towards the driving head, and a second end, which is opposite to the first end and which is suitable for engaging with the string, and said central rod is provided with at least one deformation sensor; and
 at least one absorption member, which is interposed between an end impact receiving portion of the driving head and the second end of the central rod and which is suitable for filtering a wave transmitted to the string when the end impact receiving portion of the driving head receives the impact,
 wherein the first end of the central rod is inserted into a blind hole arranged in the driving head and wherein the second end of the central rod comprises a blind hole wherein is inserted an end of the string of rods.

* * * * *